United States Patent
Ueda et al.

(10) Patent No.: US 10,052,117 B2
(45) Date of Patent: *Aug. 21, 2018

(54) JOINT SURGICAL TREATMENT

(71) Applicant: OLYMPUS CORPORATION, Tokyo (JP)

(72) Inventors: Sohei Ueda, Tokyo (JP); Chie Onuma, Tama (JP); Manabu Ishikawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 363 days.

This patent is subject to a terminal disclaimer.

(21) Appl. No.: 14/878,566

(22) Filed: Oct. 8, 2015

(65) Prior Publication Data

US 2017/0100153 A1 Apr. 13, 2017

(51) Int. Cl.
*A61B 17/32* (2006.01)

(52) U.S. Cl.
CPC .............. *A61B 17/320068* (2013.01); *A61B 2017/320072* (2013.01)

(58) Field of Classification Search
CPC ............................................ A61B 17/320068
See application file for complete search history.

(56) References Cited

U.S. PATENT DOCUMENTS

| | | | |
|---|---|---|---|
| 6,544,260 | B1 | 4/2003 | Markel et al. |
| 8,709,089 | B2 | 4/2014 | Lang et al. |
| 2004/0068267 | A1 | 4/2004 | Harvie et al. |
| 2005/0054954 | A1 | 3/2005 | Lidgren et al. |
| 2006/0030871 | A1 | 2/2006 | Hain et al. |
| 2010/0121197 | A1 | 5/2010 | Ota et al. |
| 2010/0174368 | A1 | 7/2010 | Lynch et al. |
| 2010/0191173 | A1 | 7/2010 | Kimura et al. |
| 2010/0298894 | A1 | 11/2010 | Bojarski et al. |
| 2010/0312350 | A1 | 12/2010 | Bonutti |
| 2011/0196401 | A1 | 8/2011 | Robertson et al. |
| 2012/0165843 | A1 | 6/2012 | Gannoe et al. |
| 2013/0096471 | A1 | 4/2013 | Slayton et al. |
| 2015/0165243 | A1 | 6/2015 | Slayton et al. |

FOREIGN PATENT DOCUMENTS

| | | |
|---|---|---|
| JP | H05-168642 A | 7/1993 |
| JP | 2006-334268 A | 12/2006 |

*Primary Examiner* — Andrew Yang
(74) *Attorney, Agent, or Firm* — Oliff PLC

(57) ABSTRACT

A joint surgical treatment includes bringing a treating portion of an ultrasonic device into contact with a damaged region of a cartilage that is a treated object region in the joint, and transmitting an ultrasonic vibration to the treating portion in contact with the treated object region while observing the treated object region with the arthroscope to remove the treated object region of the cartilage. The ultrasonic vibration is used to remove the treated object so as to smoothly continue a removed surface from which the treated object region is removed and a non-removed surface adjacent to the removed surface without forming any corners between the surfaces in the cartilage.

2 Claims, 7 Drawing Sheets

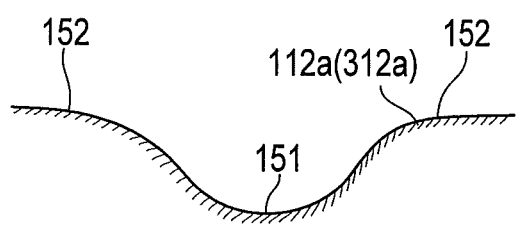
F I G. 7A
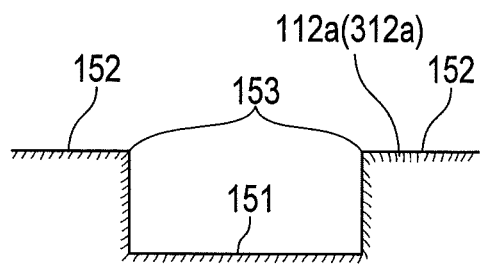
F I G. 7B

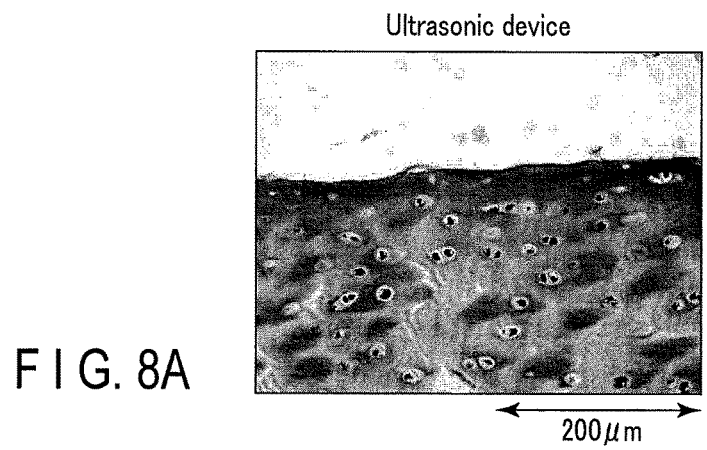
F I G. 8A  Ultrasonic device  200μm
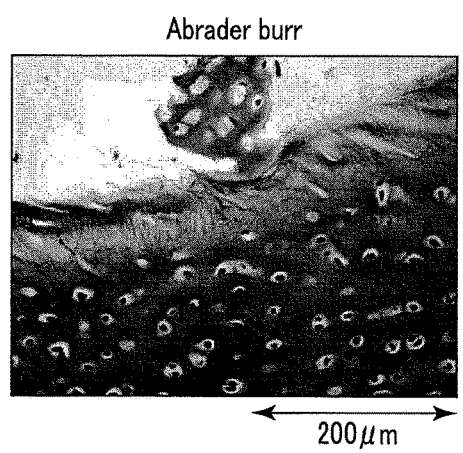
F I G. 8B  Abrader burr  200μm
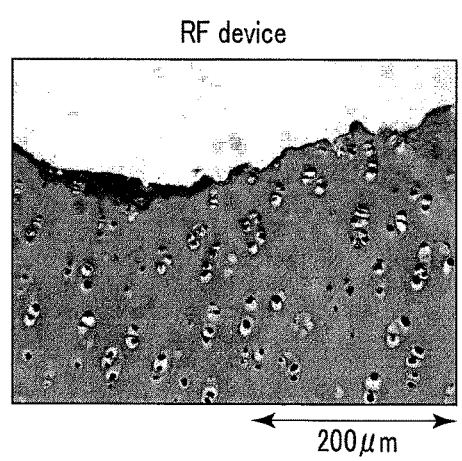
F I G. 8C  RF device  200μm

US 10,052,117 B2

JOINT SURGICAL TREATMENT

BACKGROUND OF THE INVENTION

1. Field of the Invention

The present invention relates to a joint surgical treatment to be performed under an arthroscope.

2. Description of the Related Art

It is known that, when performing an arthroscopic surgical treatment for a patient's joint, a surgeon proceeds with the treatment while inserting and removing each of treatment tools through a portal many times in accordance with a tissue of a treated region, and the above treatment tools are, for example, a shaver to shave a soft tissue, an abrader burr to abrade a bone, or an RF device to excise the soft tissue while stopping bleeding.

BRIEF SUMMARY OF THE INVENTION

According to one aspect of the invention, a joint surgical treatment which is to be performed under an arthroscope, the surgical treatment including: inserting the arthroscope and a treating portion of an ultrasonic device into a joint; bringing the treating portion of the ultrasonic device into contact with a damaged region of a cartilage that is a treated object region in the joint; and removing the treated object region of the cartilage by transmitting an ultrasonic vibration to the treating portion in a state where the treating portion is in contact with the treated object region while observing the treated object region with the arthroscope, and smoothly continuing a removed surface from which the treated object region is removed and a non-removed surface adjacent to the removed surface without forming any corners between the surfaces in the cartilage.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 7A is a schematic view showing, in a cross section, a removed surface cut off by use of an ultrasonic vibration in the treating portion of the ultrasonic treatment tool and a non-removed surface adjacent to the removed surface, in the cartilage of the knee joint (the elbow joint);

FIG. 7B is a schematic view showing, in a cross section, a removed surface cut off by an abrader burr and a non-removed surface adjacent to the removed surface, in the cartilage of the knee joint (the elbow joint);

FIG. 8A is a schematic view showing, in the form of an enlarged and observed image, a state that the cartilage of the joint is cut off in the treating portion by use of the ultrasonic vibration transmitted to the treating portion of the ultrasonic treatment tool;

FIG. 8B is a schematic view showing, in the form of an enlarged and observed image, a state that the cartilage of the joint is cut off with the abrader burr;

FIG. 8C is a schematic view showing, in the form of an enlarged and observed image, a state that the cartilage of the joint is cut off with an RF device;

DETAILED DESCRIPTION OF THE INVENTION

First Embodiment

A first embodiment according to the present invention will now be described with reference to FIG. 1 to FIG. 8C. In this embodiment, a case in which a knee joint 100 is treated is described.

Figure 1:
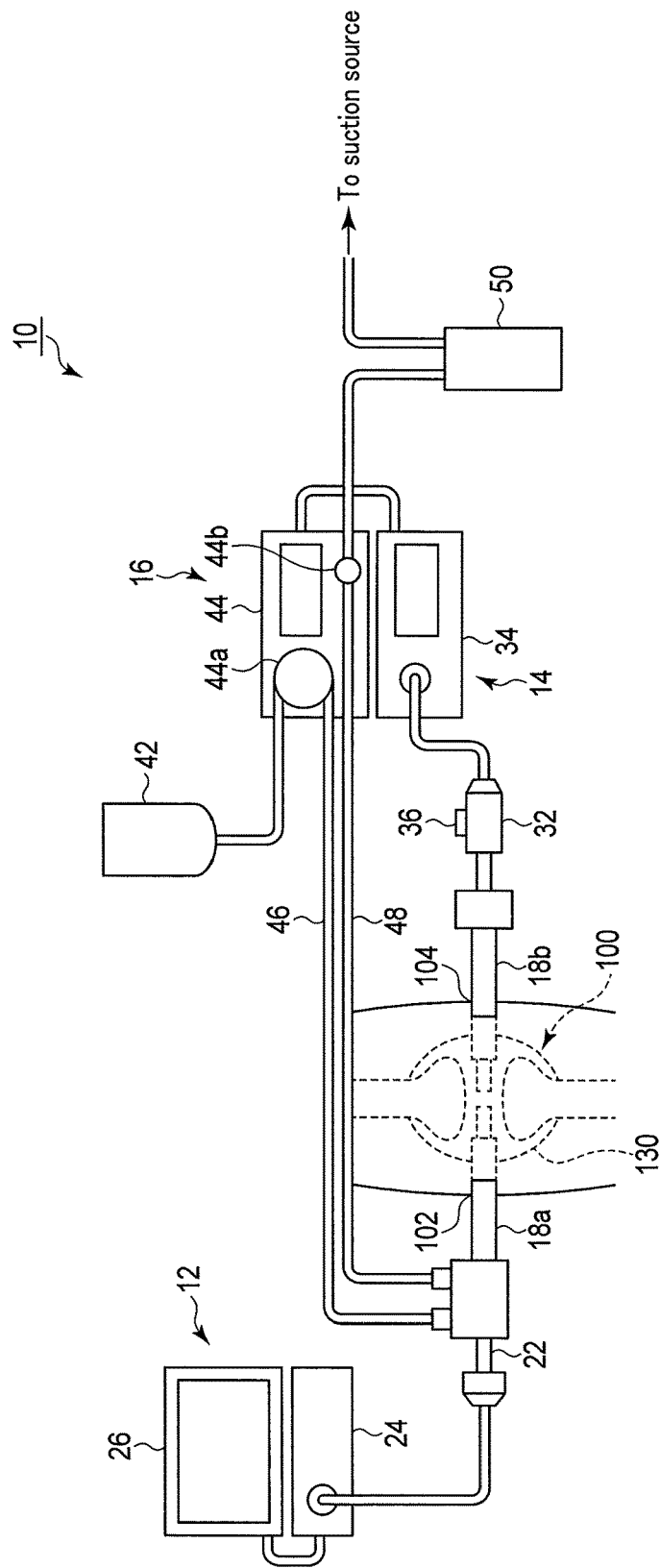
FIG. 1 is a schematic view showing a treatment system for use in a knee joint surgical treatment.

When a knee joint 100 is treated, for example, a treatment system 10 shown in FIG. 1 is used. The treatment system 10 includes an arthroscope device 12, a treatment device 14, and a perfusion device 16.

The arthroscope device 12 includes an arthroscope 22 configured to observe an inner part of the knee joint 100, i.e., the inside of a joint cavity 136 of a patient, an arthroscope controller 24 configured to perform image processing on the basis of a subject image imaged by the arthroscope 22, and a monitor 26 configured to display the image generated by the image processing in the arthroscope controller 24. The arthroscope 22 is inserted into the joint cavity 136 of the knee joint 100 through a first cannula 18a that forms a lateral portal 102 via which the inner side of the knee joint 100 of the patient communicates with an outer side of skin. It is to be noted that a position of the portal 102 is not uniform but is suitably determined in accordance with a patient's condition.

The treatment device 14 includes an ultrasonic treatment tool 32, a treatment tool controller 34, and a switch 36. Here, the treatment tool controller 34 supplies energy to the ultrasonic treatment tool 32 in accordance with an operation of the switch 36 to transmit an ultrasonic vibration to a treating portion (end effector) 68 of an after-mentioned probe 66 of the ultrasonic treatment tool 32. The treatment tool 32 is inserted into the joint cavity 136 of the knee joint 100 through a second cannula 18b that forms a medial portal 104 via which the inner side of the knee joint 100 of the patient communicates with the outer side of the skin. It is to be noted that a position of the portal 104 is not uniform but is suitably determined in accordance with the patient's condition. The switch 36 maintains, for example, a driven state of an ultrasonic transducer in a state where the switch is pressed to be operated, and when the pressed state is released, the driven state of the ultrasonic transducer is released.

Here, it is described that the one switch 36 is disposed, but the switches may be disposed. An amplitude of the ultrasonic transducer can suitably be set by the treatment tool controller 34. In consequence, by the operation of the switch 36, a frequency of the ultrasonic vibration to be output from the after-mentioned ultrasonic transducer is the same, but the amplitude may be different. Therefore, the switch 36 can suitably switch the amplitude of the ultrasonic transducer to states such as two large and small states. For example, when the amplitude can be switched to the two large and small states, the ultrasonic vibration of the small amplitude is for use in treating comparatively soft tissues such as a synovial membrane 134, cartilages 112a, 114a and 118a, and meniscuses 142 and 144. The ultrasonic vibration of the large amplitude is for use in treating comparatively hard tissues such as bones (a femur 112, a tibia 114 and a patella 118).

It is to be noted that, for example, the two switches 36 may be disposed in parallel, or a hand switch and a foot switch may selectively be used. Additionally, when the one switch 36 is switched to be used, the ultrasonic vibration of the small amplitude may be output by one operation, and the ultrasonic vibration of the large amplitude may be output by two quick pressing operations as in a double click operation of a mouse for a computer.

The perfusion device 16 includes a bag-shaped liquid source 42 that contains a perfusion liquid such as physiological saline, a perfusion pump unit 44, a liquid supply tube 46 whose one end is connected to the liquid source 42, a liquid discharge tube 48, and a suction bottle 50 to which one end of the liquid discharge tube 48 is connected. The suction bottle 50 is connected to a suction source attached to a wall of an operating room. In the perfusion pump unit 44, the perfusion liquid can be supplied from the liquid source 42 by a liquid supply pump 44a. Additionally, in the perfusion pump unit 44, suction/suction stop of the perfusion liquid in the joint cavity 136 of the knee joint 100 to the suction bottle 50 can be switched by opening/closing a pinching valve 44b as a liquid discharge valve.

The other end of the liquid supply tube 46 that is a liquid supply conduit is connected to the first cannula 18a. In consequence, the perfusion liquid can be supplied into the joint cavity 136 of the knee joint 100 via the first cannula 18a. The other end of the liquid discharge tube 48 that is a liquid discharge conduit is connected to the first cannula 18a. In consequence, the perfusion liquid can be discharged from the joint cavity 136 of the knee joint 100 via the first cannula 18a. It is to be noted that, needless to say, the other end of the liquid discharge tube 48 may be connected to the second cannula 18b, so that the perfusion liquid can be discharged from the knee joint 100.

It is to be noted that, here, the perfusion liquid can be supplied and discharged through the first cannula 18a, but a function that is capable of supplying and/or discharging the perfusion liquid may be imparted to, for example, the arthroscope 22. Similarly, the function that is capable of supplying and/or discharging the perfusion liquid may be imparted to the ultrasonic treatment tool 32. In addition, a function that is capable of supplying and discharging the perfusion liquid through the second cannula 18b may be imparted. Furthermore, the perfusion liquid may be supplied and discharged through a separate portal.

Figure 2:
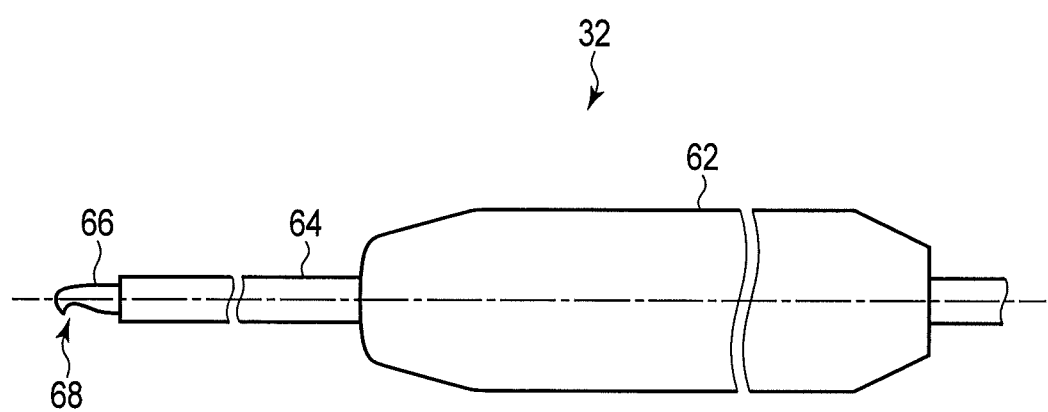
FIG. 2 is a schematic view showing one example of an ultrasonic treatment tool (an ultrasonic device) of the treatment system for use in the knee joint surgical treatment.

As shown in FIG. 2, the ultrasonic treatment tool 32 has a housing 62, a sheath 64 projected from the housing 62, and the probe 66 inserted through the sheath 64. In particular, outer peripheral surfaces of the housing 62 and the sheath 64 have insulating properties. The probe 66 is made of a metal material such as a titan alloy material capable of transmitting the ultrasonic vibration. To a proximal end of the probe 66, an unshown ultrasonic transducer unit which disposed in the housing 62 is fixed. In the ultrasonic treatment tool 32, the treating portion 68 of the probe 66 inserted through the sheath 64 is disposed together with the sheath 64 in the joint cavity 136 through the second cannula 18b. Further, when the switch 36 is pressed, energy is supplied from the treatment tool controller 34 to the ultrasonic transducer unit fixed to the proximal end of the probe 66, and the ultrasonic vibration is generated in the ultrasonic transducer. This generated ultrasonic vibration is transmitted from the proximal end of the probe 66 toward a distal side, and hence with the aid of the treating portion 68 provided in a distal portion of the probe 66, the hard tissue (the bone tissue or the like) can be resected and the soft tissue (the cartilage, a membrane tissue or the like) can be excised.

It is to be noted that a shape of the treating portion 68 can suitably be selected in accordance with a treated region. Here, there is described an example where a hook type of treating portion shown in FIG. 2 is used, but various shapes such as a rake type, a blade type and a curette type can selectively be used in consideration of an accessibility to the treated region, an adaptability to the treatment on the basis of a position, a shape, a size or the like of a cutting portion of the treating portion 68, or the like. Additionally, in the treatment of a joint (e.g., an after-mentioned elbow joint 300) other than the knee joint 100, the treating portion 68 may have a constitution where a groove is formed in a crosshatched state, or a constitution where grooves are disposed in parallel in an extending direction of the probe 66 in the treating portion 68 and each of the grooves is extended substantially perpendicular to the extending direction of the probe 66.

A structure of the knee joint 100 will briefly be described. Hereinafter, the knee joint 100 of a right knee will be described as an example.

Figure 3:
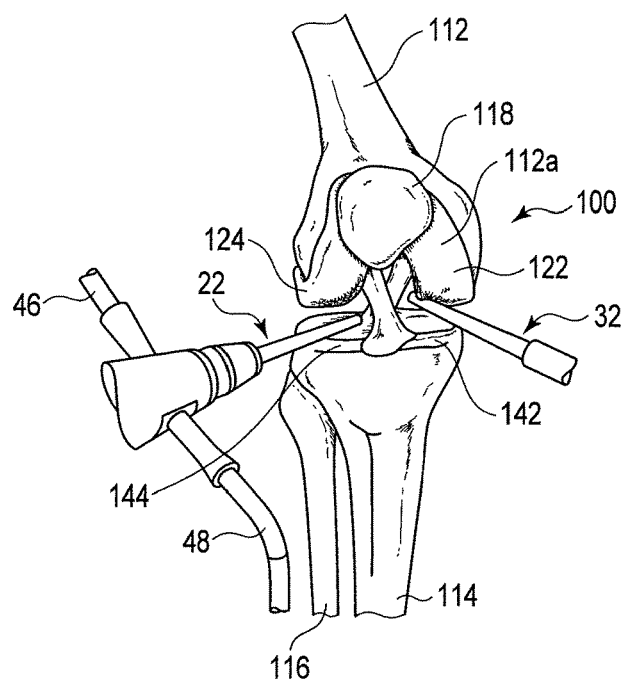
FIG. 3 is a schematic view showing a state where an arthroscope and a treating portion of the ultrasonic treatment tool are inserted from separate portals, respectively, to an articular capsule of the knee joint of a right knee seen from the anterior side.
Figure 4:
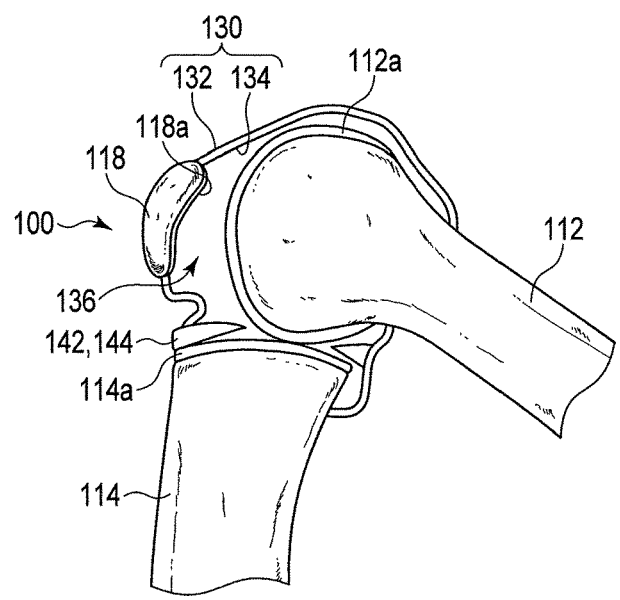
FIG. 4 is a schematic side view showing a state where the knee joint of the right knee encapsulated in the articular capsule is seen from the medial side.

As shown in FIG. 3, the knee joint 100 is mainly constituted of a femur 112, a tibia 114, a fibula 116, and a patella 118. As shown in FIG. 4, the knee joint 100 is encapsulated in a joint capsule 130. The joint capsule 130 includes a fibrous tunica 132 on an outer side, and the synovial membrane 134 on an inner side. The synovial membrane 134 forms pleats and secretes a synovial fluid, and hence the knee joint 100 smoothly moves. The inside of the joint capsule 130 is called the joint cavity 136. The joint cavity 136 is filled with the synovial fluid to be secreted from the synovial membrane 134. The joint cavity 136 of the knee joint 100 is incompletely divided into four cavities (a suprapatellar bursa, a patellofemoral joint cavity, a lateral femototibial joint cavity and a medial femototibial joint cavity), and the synovial membrane pleat is present as a partition wall between these cavities.

Additionally, in the knee joint 100, each of the cartilages (joint cartilages) 112a, 114a and 118a is present between the bones (the femur 112, the tibia 114 and the patella 118). By the cartilages 112a, 114a and 118a, impact can be absorbed in the knee joint 100, and the knee joint 100 can smoothly move.

As shown in FIG. 3, surfaces of the femur 112 which are joined to the tibia 114 are referred to as a medial condyle 122 and a lateral condyle 124, respectively. In a superior surface of the tibia 114, there are two surfaces to be joined to the medial condyle 122 and the lateral condyle 124 of the femur 112. Between the medial condyle 122 and the lateral condyle 124 of the femur 112 and the superior surface of the tibia 114, the meniscuses 142 and 144 and ligaments 152 and 154 adhere.

Figure 5:
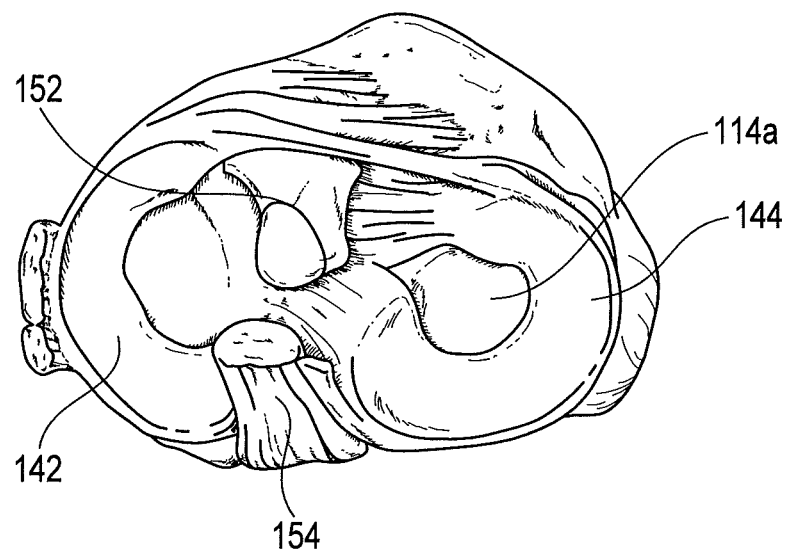
FIG. 5 is a schematic view showing a state where a medial meniscus, a lateral meniscus, an anterior cruciate ligament and a posterior cruciate ligament of the knee joint of the right knee are seen from the superior side.

As shown in FIG. 5, the meniscuses 142 and 144 form a pair on lateral and medial sides. The superior surface of the medial meniscus 142 extends along the spherical cartilage 112a disposed in the medial condyle 122 of the femur 112, and an interior surface of the medial meniscus extends along the flat cartilage 114a disposed on the superior surface of the tibia 114. Similarly, a superior surface of the lateral meniscus 144 extends along the spherical cartilage 112a disposed in the lateral condyle 124 of the femur 112, and an inferior surface of the lateral meniscus extends along the flat cartilage 114a disposed on the superior surface of the tibia 114. Consequently, the meniscuses 142 and 144 are formed so that outer edge portions of the meniscuses are thick and inner edge portions of the meniscuses are thin. It is to be noted that the outer edge portions of the medial meniscus 142 and the lateral meniscus 144 are linked to the joint capsule 130.

In the knee joint 100, an anterior cruciate ligament 152 and a posterior cruciate ligament 154 are present. When the knee joint 100 is seen from an anterior, the anterior cruciate ligament 152 is present in the anterior and the posterior cruciate ligament 154 is present in the posterior. One end of the anterior cruciate ligament 152 is passed through a space between the medial condyle 122 and the lateral condyle 124 of the femur 112 and fixed to the posterior part of the femur, and the other end of the anterior cruciate ligament is fixed to the anterior part of the superior surface of the tibia 114. The anterior cruciate ligament 152 has its start region in a posterior part of a medial surface of the lateral condyle 124 of the femur 112, and adheres to an anterior intercondylar fossa area (an end region) of the tibia 114. One end of the posterior cruciate ligament 154 is fixed to a slightly anterior region of the femur 112, and the other end of the posterior cruciate ligament is fixed to the posterior part of the superior surface of the tibia 114. The posterior cruciate ligament 154 has its start region in an anterior part of a lateral surface of the medial condyle 122 of the femur 112, and adheres to a posterior intercondylar fossa area (an end region) of the tibia 114.

Next, there will be described a method in which a surgeon uses the treatment system 10 mentioned above to perform a surgical treatment of excising a damaged region of the cartilage under the arthroscope 22 to the patient who has the damaged region in the cartilage (e.g., 112a). Here, the method of removing the deformed cartilage is only described, but may be performed together with at least one of excision of the synovial membrane 134, treatment of the damaged region of the meniscus 142 or 144, excision of the cruciate ligament 152 or 154 and cutting off of a bone (the femur 112 or the tibia 114). In this case, the treatment is performed together with at least one of the excision of the synovial membrane 134, the treatment of the damaged region of the meniscus 142 or 144, the excision of the cruciate ligament 152 or 154 and the cutting off of the bone, without removing the treating portion 68 of the same ultrasonic treatment tool 32 from the joint cavity 136 of the knee joint 100. It is to be noted that there are omitted descriptions of surgical treatments of the excision of the synovial membrane 134, the treatment of the damaged region of the meniscus 142 or 144, the excision of the cruciate ligament 152 or 154 and the cutting off of the bone.

In the knee joint 100, osteochondritis dissecans (OCD) might be caused by inflammation of the synovial membrane 134 or damages of the meniscus 142 or 144. The osteochondritis dissecans are confirmed using MRI or the like by the surgeon. Degrees of progress of the osteochondritis dissecans are indicated as, for example, grades of ICRS (International Cartilage Repair Society), i.e., Grade 0 (Normal), Grade 1 (Stable, continuity: Softened area covered by intact cartilage), Grade 2 (Partial discontinuity, stable on probing), Grade 3 (Complete discontinuity, "dead in situ", not dislocated), Grade 4 (Dislocated fragment, loose within the bed or empty defect. >10 mm in depth is B-subgroup). In the knee joint 100, the cartilages 112a are damaged in, for example, the medial condyle 122 and the lateral condyle 124 of the femur 112 due to the osteochondritis dissecans.

In the treatment, the instrument such as an ultrasonic cannula, surgical knife or the like to form the portals 102 and 104 in the knee joint 100, and an instrument such as the treatment system 10 or the like for use in a surgical treatment of excising the cartilage and the bone. It is to be noted that the treating portion 68 of the ultrasonic treatment tool 32 is formed into the suitable shape, e.g., the hook type.

Further, the surgeon forms the portal 102, and disposes a distal end of the arthroscope 22 in the joint cavity 136 of the knee joint 100 of the right knee (may be a left knee) of the patient through the first cannula 18a to be disposed in the portal 102. Additionally, the surgeon forms the portal 104, and disposes the treating portion 68 of the ultrasonic treatment tool 32 in the joint cavity 136 of the knee joint 100 through the second cannula 18b to be disposed in the portal 104. In this case, the surgeon uses the perfusion device 16 to fill the joint cavity 136 of the knee joint 100 of the patient with physiological saline.

In this state, the surgeon uses the arthroscope 22 to suitably observe the inside of the joint cavity 136 of the knee joint 100. In this case, the surgeon observes a condition of the cartilage in the joint cavity 136 of the knee joint 100. For example, when the cartilage 112a adhered to the medial condyle 122 of the femur 112 is damaged, the surgeon confirms the grade of the osteochondritis dissecans with the arthroscope 22. By use of the arthroscope 22, the surgeon confirms whether a part of the cartilage 112a is softened (Grade 1), whether laceration such as partial tear is present in a part of the cartilage 112a (Grade 2), whether a part of the cartilage 112a is discontinued from a bone (the medial condyle 122 of the femur 112) to which the cartilage 112a adheres (Grade 3), or whether a bone cartilage piece is liberated and the bone (the medial condyle 122 of the femur 112) having been hidden behind the cartilage 112a is exposed (Grade 4), to judge the grade. Additionally, in each of Grades 1 to 4, presence/absence of the bone spurs and presence/absence of hardened regions are confirmed in the medial condyle 122 and the lateral condyle 124 of the femur 112.

Figure 6:
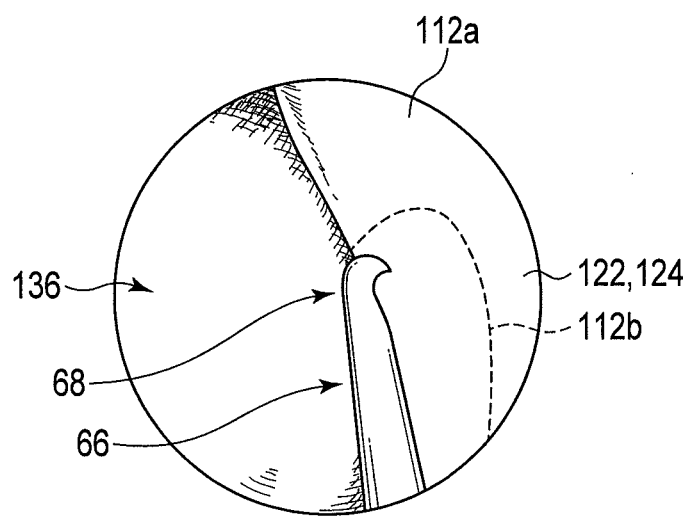
FIG. 6 is a schematic view showing a state where the ultrasonic vibration is transmitted to the treating portion of the ultrasonic treatment tool to remove a treated object region of the cartilage of the knee joint (elbow joint) under the arthroscope.

Further, as shown in FIG. 6, the treating portion 68 of the ultrasonic treatment tool 32 is brought into contact with the treatment object region (e.g. the damaged region of the cartilage 112a) while observing the treated object region always disposed in the view field of the arthroscope 22. In this state, the switch 36 is operated to suitably perform the treatment to the treatment object region by use of the ultrasonic vibration. At this time, as shown in FIG. 7A, the surgeon can easily form the treated surface by the treating portion 68 of the ultrasonic treatment tool 32 to which the ultrasonic vibration is transmitted, as the smooth surface without forming any corner portions therein, by suitably moving the treating portion 68 in accordance with the movement of the probe 66 in the axial direction. In consequence, the region treated with the treating portion 68 of the ultrasonic treatment tool 32 by the surgeon is hard to be stuck on another region.

When the surgeon judges that a condition of a part of the cartilage 112a is Grade 1, the treating portion 68 of the ultrasonic treatment tool 32 is opposed to a softened region (a treated object region) 112b of the cartilage 112a as shown in FIG. 6. Further, as required, the softened region 112b of the cartilage 112a is removed by moving the treating portion 68 along the axial direction of the probe 66 while transmitting the ultrasonic vibration to the treating portion 68 of the ultrasonic treatment tool 32. When the softened region 112b of the cartilage 112a is removed, the treatment is performed so that any corners are not left in the cartilage 112a as shown in FIG. 7A. Additionally, in Grade 1, when a bone spur (not shown) is formed in the medial condyle 122 of the femur 112, the bone spur is removed by transmitting the ultrasonic vibration to the treating portion 68 of the same ultrasonic treatment tool 32.

It is to be noted that by the operation of the switch 36, an amplitude of an ultrasonic transducer in excising the softened region 112b of the cartilage 112a may be different from an amplitude in excising the osteophyte of the medial condyle 122 of the femur 112. This also applies to a case where the surgeon treats a region judged to be Grade 2 to Grade 4. Additionally, in the same manner as in the case where the softened region 112b of the cartilage 112a is removed, as to the treated object region, the treatment is performed so that any corners are not left in the cartilage 112a as shown in FIG. 7A also in a case where the surgeon treats the region judged to be Grade 2 to Grade 4.

Here, when the surgeon judges that a condition of a part of the cartilage 112a is Grade 2, as shown in FIG. 6, the treating portion 68 of the ultrasonic treatment tool 32 is faced to a torn region (a treated object region) 112b of the cartilage 112a. Further, the torn region of the cartilage 112a is removed by moving the treating portion 68 along the axial direction of the probe 66 while transmitting the ultrasonic vibration to the treating portion 68 of the ultrasonic treatment tool 32. In addition, the bone spur formed in Grade 2 is removed by transmitting the ultrasonic vibration to the treating portion 68 of the ultrasonic treatment tool 32. Also at this time, the treatment is performed without leaving any corner portions in treated regions of the cartilage 112a and the medial condyle 122 of the femur 112.

When the surgeon judges that the condition of a part of the cartilage 112a is Grade 3, as shown in FIG. 6, the treating portion 68 of the ultrasonic treatment tool 32 is opposed to the torn region (the treated object region) 112b of the cartilage 112a and a torn region of the medial condyle 122 of the femur 112. Further, the torn region 112b of the cartilage 112a and the torn region of the medial condyle 122 of the femur 112 are removed together with the bone spurs formed in the medial condyle 122 of the femur 112 and the like, by moving the treating portion 68 along the axial direction of the probe 66 while transmitting the ultrasonic vibration to the treating portion 68 of the ultrasonic treatment tool 32. Also at this time, the treatment is performed without leaving any corner portions in the treated regions of the cartilage 112a and the medial condyle 122 of the femur 112.

When the surgeon judges that the condition of a part of the cartilage 112a is Grade 4, the torn region (the treated object region) 112b of the cartilage 112a shown in FIG. 6 might peel from the medial condyle 122 of the femur 112. In this case, when the bone (the medial condyle 122 of the femur 112) under the cartilage 112a undergoes necrosis due to an interruption in circulation of blood or the like, the bone cartilage piece separates to be liberated as a loose body in the joint capsule 130. In addition, the loose body might be separated also from the cartilage 112a in the joint capsule 130. In such a case, the treating portion 68 of the ultrasonic treatment tool 32 is faced to the torn region 112b of the cartilage 112a and the torn region of the medial condyle 122 of the femur 112. Further, the torn region 112b of the cartilage 112a and the torn region of the medial condyle 122 of the femur 112 are removed together with the osteophyte formed in the medial condyle 122 of the femur 112, by moving the treating portion 68 along the axial direction of the probe 66 while transmitting the ultrasonic vibration to the treating portion 68 of the ultrasonic treatment tool 32. Also at this time, the treatment is performed without leaving any corner portions in the treated regions of the cartilage 112a and the medial condyle 122 of the femur 112. It is to be noted that the region (arthrosis loose body) liberated from the cartilage 112a is sucked or curetted to be removed. Further, excision or curettage of the deformed cartilage 112a, removal of the liberated cartilage piece, and grafting of the cartilage 112a are carried out. For example, when the bone cartilage piece is grafted, a region to be grafted needs to be dissected. In this case, the ultrasonic vibration is transmitted to the treating portion 68 of the ultrasonic treatment tool 32, thereby carrying out the dissection. Further, the bone cartilage piece is fixed by a known method.

Thus, in accordance with the condition, the treating portion 68 is moved along the axial direction of the probe 66 while transmitting the ultrasonic vibration to the treating portion 68 of the ultrasonic treatment tool 32, to suitably dissect the cartilage 112a. In addition, the ultrasonic vibration is transmitted to the treating portion 68 of the same ultrasonic treatment tool 32, to remove the bone spur.

Here, there has been described the example where the cartilage 112a of the femur 112 and the femur 112 are treated, but the inferior cartilage 118a (see FIG. 4) of the patella 118 in chondromalacia patellae can similarly be treated.

As described above, the technique of removing the damaged region 112b of the cartilage (e.g. 112a) under the arthroscope 22 can be considered as follows.

By use of the treatment system 10, the surgeon can perform a series of treatment of removing the treated object region of the cartilage 112a and the femur 112 with the treating portion 68 of the treatment tool 32 while the one ultrasonic treatment tool 32 is disposed and retained in the second cannula 18b. Consequently, by use of the treatment system 10, the surgeon can perform a series of treatment of removing the treated object region of the cartilage 112a and the femur 112, together with excising the synovial membrane 134 and excising the damaged region of the meniscus 142 or 144, with the treating portion 68 of the treatment tool 32 while the one ultrasonic treatment tool 32 is disposed and retained in the second cannula 18b.

Further, the surgeon has heretofore replaced and used different instruments to the portal 104 by, for example, using the radio frequency device (RF device) or the like in a smoothening treatment of the cartilage 112a which is a soft tissue and using the abrader burr or the like in the smoothening treatment of the femur 112, the tibia 114 or the patella 118 which are hard tissues. In this embodiment, when the treated object regions 112b of the cartilage 112a and the femur 112 are removed, the ultrasonic treatment tool 32 does not have to be replaced to the portal 104. These treatments can be performed with the one ultrasonic treatment tool 32. Consequently, during the surgical treatment, the surgeon does not have to replace the treatment tool 32 disposed in the joint cavity 136, and hence the surgical treatment time can be shortened.

In addition, an abrader burr has a structure to abrade the bone or the like by periaxial rotation. Therefore, a head portion of the abrader burr is formed to be larger (thicker) than the treating portion 68 of the ultrasonic treatment tool 32 in the same manner as in a shaver that has heretofore been used in excising the synovial membrane 134. On the other hand, when the treatment is performed by using the ultrasonic treatment tool 32, the treating portion 68 does not have to be rotated, and hence the treating portion 68 can be formed in a suitable shape and the treating portion 68 can be formed to be smaller as compared with the case where the shaver or the abrader burr is used. Consequently, in the treatment in which the ultrasonic treatment tool 32 is used, a movable range of the treating portion 68 with respect to the cannula 18b increases. Therefore, as compared with the case where the shaver or the abrader burr is used, treatment regions such as posterior surfaces of the medial condyle 122 and the lateral condyle 124 of the femur 112 or a treatment region of an inferior surface of the patella 118 can easily be approached.

The abrader burr abrades the bone (the bone spur) that is the hard tissue by the periaxial rotation, and hence loads that act on the abrader burr increase in a case where the bone is abraded. Consequently, the abrader burr might noticeably entirely be vibrated (suwung) by the loads onto the treating portion. On the other hand, the treating portion 68 of the ultrasonic treatment tool 32 is not periaxially rotated but the bone can be resected only by moving (vibrating) the treating portion in the axial direction of the probe 66. Consequently, loads that act on the housing 62 or the like through the treating portion 68 are small in a case where the bone is resected by the treating portion 68. In consequence, the ultrasonic treatment tool 32 inserted into the joint cavity 136 of the knee joint 100 through the portal 104 does not noticeably vibrate. That is, in the case where the bone is resected by the treating portion 68, leaping of the treating portion 68 due to the rotary motion as in the abrader burr is not caused, and hence damages of the peripheral tissue can be decreased.

In addition, the abrader burr performs the cutting off by the periaxial rotation as described above, and hence, when the cartilage is cut off with the abrader burr, a cut-off surface of the cartilage tends to be made fluffy as shown in FIG. 8B. Consequently, when the cartilage is abraded with the abrader burr, it is difficult to smoothen the cut-off surface and it is easier to generate concave and convex areas in the excised region. In addition, when the cartilage 112a is cut off with the abrader burr, as shown in FIG. 7B, a corner 153 is formed between a removed surface 151 from which the cartilage (112a) is removed and each of non-removed surfaces 152 adjacent to the removed surface 151.

On the other hand, in the case where the cartilage is cut off with the treating portion 68 of the ultrasonic treatment tool 32, as shown in FIG. 8A, a more precise and smoother treated surface (the removed surface) can be formed than in the case where the shaver or the abrader burr is used. In consequence, the excised region of the cartilage (112a) by the treating portion 68 of the ultrasonic treatment tool 32 has less concave and convex areas and is smoothened. In addition, when the cartilage (112a) is cut off with the ultrasonic treatment tool 32, as shown in FIG. 7A, a region between the removed surface 151 from which the cartilage (112a) is removed and each of the non-removed surfaces 152 adjacent to the removed surface 151 is continuous as a smooth surface in which any corners are not formed. Further, the cartilage (e.g., 112a) and the bone (e.g., the medial condyle 122 of the femur 112) to which the cartilage adheres are removed to form the removed surface 151, whereby a dented region having a substantially circular cross section is formed on the removed surface.

As described above, the cartilage is excised with the treating portion 68 by use of the ultrasonic vibration, and hence the excised region of the cartilage is smoothened. Consequently, when the surgeon performs the treatment by use of the ultrasonic treatment tool 32 and then the patient bends and stretches the knee joint 100 to move the femur 112, the tibia 114 and the patella 118, the femur 112, the tibia 114 and the patella 118 can be prevented from being stuck on one another, which can contribute to a smooth joint movement.

In addition, when a radio frequency device is used to remove the cartilage, heat is generated by a radio frequency current flowing through the cartilage. Consequently, as shown in FIG. 8C, there is the fear that the cartilage is invaded by heat.

On the other hand, the cartilage is cut off with the ultrasonic treatment tool 32 by use of the ultrasonic vibration, and hence the radio frequency current does not flow through the cartilage. Consequently, in the cartilages (112a, 114a and 118a) and the bones (the femur 112, the tibia 114 and the patella 118) adjacent to the cartilages, a normal region is less invaded by heat, and thermal necrosis is prevented from being caused to the cartilages (112a, 114a and 118a).

Modification

Figure 9:
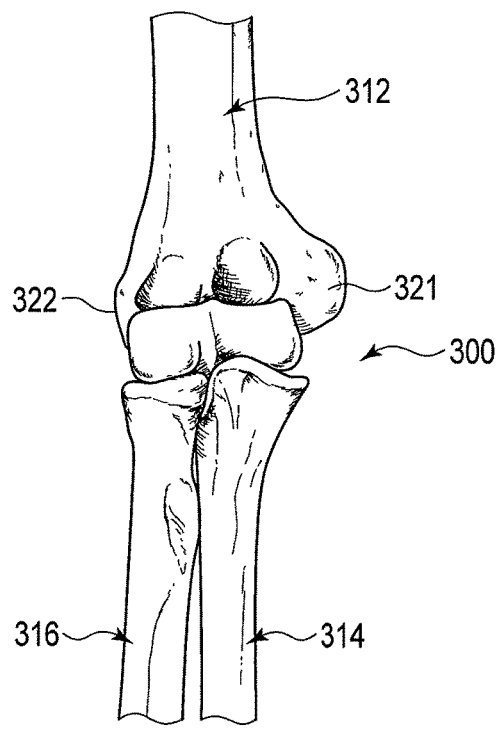
FIG. 9 is a schematic view of a right elbow joint seen from an anterior side of a human body.
Figure 10:
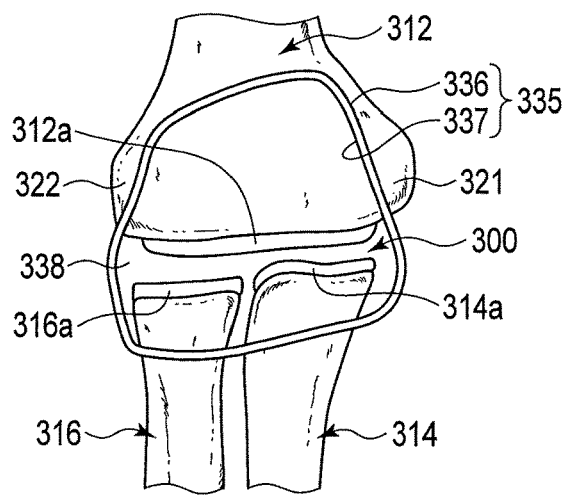
FIG. 10 is a schematic view schematically showing the right elbow joint together with the articular capsule.

It is to be noted that in one example, the treating portion (the end effector) 68 of the ultrasonic treatment tool 32 mentioned above excises the cartilage and the bone adjacent to the cartilage in the elbow joint 300 by use of the ultrasonic vibration. As shown in FIG. 9 and FIG. 10, the elbow joint 300 is formed of a humerus 312, an ulna 314, and a radius 316. The humerus 312 has a medial epicondyle 321, and a lateral epicondyle 322 on an elbow joint 300 side.

As like the knee joint 100, the elbow joint 300 is encapsulated in the joint capsule 335. The joint capsule 335 is formed of an outer fibrous tunica 336 and the inner synovial membrane 337. The synovial membrane 337 forms pleats and secretes a synovial fluid, and hence the elbow joint 300 smoothly moves. The inside of the joint capsule 335 is called the joint cavity 338, and the joint cavity 338 is filled with the synovial fluid to be secreted from the synovial membrane 337. The joint cavity 338 of the elbow joint 300 is incompletely divided into two anterior and posterior cavities.

Additionally, in the elbow joint 300, each of the cartilages 312a, 314a and 316a is present between the bones (the humerus 312, the ulna 314 and the radius 316). The cartilage 312a is disposed on an inferior surface of the humerus 312. Further, the cartilage 314a is disposed on a superior surface of the ulna 314, and the cartilage 316a is disposed on a superior surface of the radius 316.

In the elbow joint 300, osteochondritis dissecans (OCD), which are described in the description of the treatment of the knee joint 100, might be caused by the little league elbow. In the elbow joint 300, the cartilages 312a are damaged in, for example, the lateral epicondyle 322 of the humerus 312 due to the osteochondritis dissecans.

In the treatment of removing the damaged region of the cartilage (312a) in the elbow joint 300 under the arthroscope 22, in the same manner as in the knee joint 100, a distal end of the arthroscope 22 is disposed in the joint cavity 338 of the elbow joint 300 of the right elbow (may be a left elbow) through the first cannula 18a to be disposed in the portal 302. Further, the treating portion 68 of the ultrasonic treatment tool 32 is disposed in the joint cavity 338 of the elbow joint 300 through the second cannula 18b to be disposed in the portal 304. In this case, the perfusion device 16 is used to fill the joint cavity 338 of the elbow joint 300 with physiological saline while performing the suction.

Here, in the vicinity of the elbow joint 300, a lot of nerves (an elbow radius nerve, an ulna nerve, a median nerve and the like) run. Therefore, it is necessary to form the portals 102 and 104 without damaging the nerves. Therefore, one of a proximal anterolateral portal, a distal anterolateral portal, a direct lateral portal, an anteromedial portal, a proximal medial portal, a straight posterior portal and a posterolateral portal is employed as the portal 102 or 104. It is determined which one of the abovementioned portals is to be employed as the portal 102 or 104, on the basis of a position of the cartilage to be removed (i.e., a position of the treated object region).

When the distal end of the arthroscope 22 is disposed in the joint cavity 338 a condition of the cartilage in the joint cavity 338 of the elbow joint 300 is observed. For example, when the cartilage 312a is damaged in the lateral epicondyle 322 of the humerus 312, a grade of the osteochondritis dissecans is confirmed with the arthroscope 22. Further, in the same manner as in the knee joint 100, the treating portion 68 of the ultrasonic treatment tool 32 is brought into contact with a treated object region of the cartilage (312a) while observing the treated object region always in a view field of the arthroscope 22. The ultrasonic vibration is transmitted to the treating portion 68 in a state where the treating portion 68 is in contact with the treated object region, the cartilage (e.g., 312a) and a bone (e.g., the lateral epicondyle 322 of the humerus 312) adjacent to the cartilage are excised in the elbow joint 300.

Also in the present modification, the cartilage and the bone to which the cartilage adheres are excised by the ultrasonic vibration in the same manner as in the knee joint 100, and hence an excised region of the cartilage (312a) by the treating portion 68 of the ultrasonic treatment tool 32 has less concave and convex areas and is smoothened. Consequently, when the cartilage (312a) is cut off with the ultrasonic treatment tool 32, a region between the removed surface 151 from which the cartilage (312a) is removed and each of the non-removed surfaces 152 adjacent to the removed surface 151 is continuous as a smooth surface in which any corners are not formed. Further, the cartilage (e.g., 312a) and the bone (e.g., the lateral epicondyle 322 of the humerus 312) to which the cartilage adheres are removed to form the removed surface 151, whereby a dented region having a substantially circular cross section is formed on the removed surface.

Additionally, also in the present modification, the cartilage is cut off with the ultrasonic treatment tool 32 by use of the ultrasonic vibration, and hence the high frequency current does not flow through the cartilage. Consequently, in the cartilages (312a, 314a and 316a) and the bones (the humerus 312, the ulna 314 and the radius 316) adjacent to the cartilages, a normal region is less invaded by heat, and thermal necrosis is prevented from being caused to the cartilages (312a, 314a and 316a).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A joint surgical treatment which is to be performed under an arthroscope, the surgical treatment comprising:
    inserting the arthroscope and a treating portion of an ultrasonic device into a joint;
    bringing the treating portion of the ultrasonic device into contact with a damaged region of a cartilage that is a treated object region in the joint; and
    removing the treated object region of the cartilage by transmitting an ultrasonic vibration to the treating portion in a state where the treating portion is in contact with the treated object region while observing the treated object region with the arthroscope, and smoothly continuing a removed surface from which the treated object region is removed and a non-removed surface adjacent to the removed surface without forming any corners between the surfaces in the cartilage.

2. The surgical treatment according to claim 1, wherein the removing the damaged region of the cartilage by the ultrasonic vibration includes forming a dented region having a substantially circular cross section on the removed surface.

* * * * *